United States Patent
Oko et al.

(10) Patent No.: US 11,389,262 B2
(45) Date of Patent: *Jul. 19, 2022

(54) MODULAR POST AND PARTITION ASSEMBLY FOR EQUIPMENT STERILIZATION

(71) Applicant: K1 Medical Technologies, LLC, Woodbridge, CT (US)

(72) Inventors: Walter J. Oko, Woodbridge, CT (US); Scott E. Cohen, Woodbridge, CT (US)

(73) Assignee: K1 Medical Technologies, LLC, Woodbridge, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/323,210

(22) Filed: May 18, 2021

(65) Prior Publication Data
US 2021/0267708 A1    Sep. 2, 2021

Related U.S. Application Data

(63) Continuation of application No. 16/522,488, filed on Jul. 25, 2019, now Pat. No. 11,090,127.

(60) Provisional application No. 62/711,195, filed on Jul. 27, 2018.

(51) Int. Cl.
*A61B 50/33* (2016.01)
*A61B 50/22* (2016.01)
*A61L 2/26* (2006.01)

(52) U.S. Cl.
CPC .............. *A61B 50/33* (2016.02); *A61B 50/22* (2016.02); *A61L 2/26* (2013.01); *A61L 2202/182* (2013.01); *A61L 2202/24* (2013.01)

(58) Field of Classification Search
CPC ......... A61B 19/02; A61B 50/22; A61B 50/23; A61B 50/33; A61L 2/07; A61L 2/26; A61L 2200/18; A61L 2200/182; A61L 2202/24; E04H 1/00; E04H 3/00; E04H 5/00; E04H 17/00; E04H 17/10; E04H 17/16
See application file for complete search history.

(56) References Cited

U.S. PATENT DOCUMENTS

| | | | |
|---|---|---|---|
| 3,067,903 | A | 12/1962 | Jones, Jr. |
| 4,458,461 | A | 7/1984 | Holley |
| 4,798,292 | A | 1/1989 | Hauze |
| 5,069,263 | A | 12/1991 | Edwards |

(Continued)

FOREIGN PATENT DOCUMENTS

EP          1156178 A2 * 11/2001 ........... E04H 17/168

OTHER PUBLICATIONS

PCT International Search Report and Written Opinion dated Oct. 22, 2019, for PCT Patent Application No. PCT/US2019/043503.
Ensinger GmbH, Tecapro®, https://www.ensingerplastics.com/en-US/shapes/products/pp-medical-tecapro-mt-white.

(Continued)

*Primary Examiner* — Bryon P Gehman
(74) *Attorney, Agent, or Firm* — McCarter & English, LLP (57) ABSTRACT

The present disclosure provides advantageous post and partition assembly that is configured and adapted to promote modularity and withstand the harsh environment of central sterile processing processes. Modular post assembly may be removed and relocated on tray without additional fasteners or components. Tray and bracket assembly may further provide identification features to correctly associate cataloged reusable medical devices to identified trays.

19 Claims, 10 Drawing Sheets

(56) References Cited

U.S. PATENT DOCUMENTS

| | | | |
|---|---|---|---|
| 5,167,433 | A | 12/1992 | Ryan |
| 6,244,447 | B1 | 6/2001 | Frieze et al. |
| 6,382,575 | B1 | 5/2002 | Frush et al. |
| 6,585,942 | B1 | 7/2003 | Bussell et al. |
| 8,827,088 | B1 | 9/2014 | Krause et al. |
| 10,391,190 | B1 | 8/2019 | Oko et al. |
| 2005/0249651 | A1 | 11/2005 | Riley |
| 2006/0228980 | A1 | 10/2006 | Hammond |
| 2006/0266666 | A1 | 11/2006 | Bettenhausen et al. |
| 2008/0257897 | A1 | 10/2008 | Mcalpine et al. |
| 2008/0314789 | A1 | 12/2008 | Thomas |
| 2010/0123113 | A1 | 5/2010 | Young |
| 2014/0083886 | A1 | 3/2014 | Winterrowd et al. |
| 2014/0346068 | A1 | 11/2014 | Omura et al. |

OTHER PUBLICATIONS

Solvay S.A., Radel®, https://www.solvay.com/en/brands/radel-ppsu.
U.S. Food and Drug Administration, "How to Determine if Your Product is a Medical Device," Dec. 16, 2019, https://www.fda.gov/medical-devices/classify-your-medical-device/how-determine-if-your-product-medical-device.
Westlake Plastics, Propylux®, https://www.westlakeplastics.com/product-family/propylux.
U.S. Appl No. 62/633,429, filed Feb. 21, 2018.
U.S. Appl. No. 62/711,195, filed Jul. 27, 2018.
U.S. Appl. No. 16/522,488, filed Jul. 25, 2019, U.S. Pat. No. 11,090,127.
PCT/US2019/043503, Jul. 25, 2019, WO/2020/023785.

\* cited by examiner

MODULAR POST AND PARTITION ASSEMBLY FOR EQUIPMENT STERILIZATION

CROSS-REFERENCE TO RELATED APPLICATION

The present application is a continuation application that claims priority benefit to a U.S. non-provisional patent application entitled "Modular Post and Partition Assembly for Equipment Sterilization," which was filed on Jul. 25, 2019 and assigned Ser. No. 16/522,488, and which claimed priority to a U.S. provisional patent application entitled "Modular Post and Partition Assembly for Equipment Sterilization," which was filed on Jul. 27, 2018 and assigned Ser. No. 62/711,195. Applicant incorporates herein by reference the content of the foregoing provisional and non-provisional patent applications.

FIELD OF THE DISCLOSURE

The present disclosure generally relates to tray mountable post and partition and, more generally, a modular sterilization tray and post/partition system for detachably retaining reusable medical devices.

BACKGROUND OF THE DISCLOSURE

Sterilization trays provide a container for retaining reusable medical devices during a patient's surgical procedure (e.g., during the perioperative process, which may include preoperative care, intraoperative care, and postoperative care) and/or during the central sterile processing process (e.g., autoclave-based steam sterilization). Included within the central sterile processing process are the steps of decontamination, cleaning, assemble and pack, sterilization, storage, distribution/transportation, and aseptic presentation. In hospitals and other health care facilities, a sterile processing department (e.g., Central Sterile Services Department) performs sterilization and other actions on medical devices, equipment, and consumables for subsequent use by medical professionals in the operating room of the hospital (or other health care facility) and also for other aseptic procedures.

Sterilization trays may include a cover, a base, and one or more attachment mechanisms for retaining reusable medical devices. After central sterile processing, sterilization trays may be brought into the operating room, or other venue, to provide a "tool box" for medical professionals to work out of. Despite being used by medical professionals as a "tool box", sterilization trays provide no feedback, instruction, or ease of modularity to assist medical professionals.

Based on the foregoing, a need exists for an effective modular "tool box" that offers flexibility and reliability in the positioning of reusable medical devices in connection with the perioperative process, the central sterile processing process, and/or subsequent access to/use of the sterilized reusable medical devices. Thus, an interest exists for modular sterilization trays and brackets, and related methods of use. These and other inefficiencies and opportunities for improvement are addressed and/or overcome by the assemblies, systems and methods of the present disclosure.

SUMMARY OF THE DISCLOSURE

The present disclosure provides an advantageous assembly for detachably retaining devices relative to a container (e.g., a tray). In particular, the present disclosure is directed to systems/methods for detachably retaining reusable medical devices and other instruments during the perioperative process and/or during the central sterile processing process. Even more particularly, exemplary assemblies are disclosed that include a tray with at least one modular post/partition (e.g., bracket and divider) assembly mounted directly or indirectly thereto, for detachable retention of reusable medical devices and/or instruments to facilitate use/exposure during the perioperative process and the central sterile processing process.

As used throughout, the term "reusable medical device," "medical device," or any combination thereof, includes an instrument, apparatus, implement, machine, contrivance, implant, in vitro reagent, or other similar or related article, including a component part, accessory, lab equipment, reagent, or test kit, as will be known to a person skilled in the art. The above definition of a reusable medical device is intended to be broader than the definition provided by the United States Food and Drug Administration (e.g., https://www.fda.gov/MedicalDevices/DeviceRegulationandGuidance/Overview/ClassifyYourDevice/ucm051512.htm). Although the reusable medical device is referenced for use during surgery, additional instruments and/or devices that require central sterile processing, but are not used in connection with surgery, are expressly included in the present disclosure. Central sterile processing may include autoclave steam sterilization, which combines heat, humidity, and elevated pressure to sterilize a medical device. As used herein, a "user" generally refers to a human or a non-human and, in the case of a non-human, the term "user" generally refers to systems and devices that constitute and/or are controlled, in whole or in part, by software, artificial intelligence, robots and/or recognition software/machines.

In exemplary embodiments, the present disclosure provides an advantageous modular post and partition (e.g., bracket and divider) assembly that is configured and adapted to detachably interface with a tray and further withstand the harsh environment of a central sterile processing process. As used herein, modular post and partition assembly may be alternatively referred to as "modular post assembly," "modular partition assembly," "modular bracket assembly," "modular divider assembly," "post assembly," "bracket assembly," "divider assembly," among other logical variations, as will be understood in view of this disclosure. Based on this disclosure, it should be understood that "modular post assembly" and "post assembly" further include at least one partition (e.g., bracket and divider). Exemplary modular post assemblies according to the present disclosure may be removed and relocated relative to a tray without additional fasteners or components. The disclosed post and partition assembly may further provide identification features to associate cataloged reusable medical devices to identified trays.

Any combination or permutation of features, functions and/or embodiments as disclosed herein is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

BRIEF DESCRIPTION OF DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure.

To assist those of ordinary skill in the art in making and using the disclosed assemblies, systems and methods, reference is made to the appended figures, wherein.

DETAILED DESCRIPTION OF DISCLOSURE

The exemplary embodiments disclosed herein are illustrative of advantageous mounting assemblies (e.g., assemblies/devices for detachable retention of reusable medical devices during the perioperative process and/or during the central sterile processing process), and systems of the present disclosure and methods/techniques thereof. It should be understood, however, that the disclosed embodiments are merely illustrative of the present disclosure, which may be embodied in various forms. Therefore, details disclosed herein with reference to exemplary assemblies/fabrication methods and associated processes/techniques of assembly and use are not to be interpreted as limiting, but merely as the basis for teaching one skilled in the art how to make and use the advantageous assemblies/systems of the present disclosure.

The present disclosure provides an advantageous assembly for detachably retaining and/or containing reusable medical devices and other devices relative to a tray. In particular, the present disclosure is directed to systems/methods for detachably retaining reusable medical devices and other instruments during the perioperative process and/or during the central sterile processing process. Even more particularly, exemplary assemblies are disclosed that include a tray with at least one modular post and partition assembly mounted directly or indirectly thereto, for detachable retention of reusable medical devices and/or instruments to facilitate use/exposure during the perioperative process and/or during the central sterile processing process.

In exemplary embodiments, the present disclosure provides an advantageous modular post and partition assembly that is configured and adapted to detachably interface with a tray and further withstand the harsh environment of a central sterile processing process. Exemplary modular post assemblies of the present disclosure may be removed and relocated relative to a tray without additional fasteners or components. The disclosed post assemblies may further provide identification features to correctly associate cataloged reusable medical devices to identified trays.

The disclosed post may include engagement features to accommodate at least one partition (e.g., bracket and divider). Partition may include corresponding engagement features to releasably engage with the disclosed post. Engagement with the disclosed post may be accomplished without fasteners. The disclosed tray may further include similar post engagement features to capture at least one partition (e.g., bracket and divider). In an exemplary embodiment, the post/partition assembly may include at least two posts and at least one partition (e.g., bracket and divider). In another exemplary embodiment, the disclosed post may capture about four partitions (e.g., brackets and dividers). In some embodiments, the angle between one post engagement feature, in comparison to an adjacent post engagement feature, is substantially similar. In exemplary embodiments, the angle between each of the adjacent post engagement features is between about 20 degrees to about 180 degrees, which further defines a range of about 45 degrees to about 90 degrees. In some embodiments, at least two post engagement features may be situated such that when at least two partitions are installed, the at least two partitions are substantially parallel.

As used herein, "partition" may refer to a bracket or a divider. The functionality of the various partitions will be better understood with reference to the figures and this disclosure. Additional partition designs may be utilized, as described in U.S. Provisional Application No. 62/633,429, which is incorporated herein by reference.

Referring now to the drawings, like parts are marked throughout the specification and drawings with the same reference numerals, respectively. Drawing figures are not necessarily to scale and in certain views, parts may have been exaggerated or removed for purposes of clarity.

With reference to FIGS. 1A-1E, advantageous post 10 may include body 12 and tray attachment feature (e.g., clip) 14. Body 12 and clip 14 may be fabricated to form a unitary component (e.g., molding, casting, extruding) or may be assembled together from individual components. In one embodiment, where body 12 and clip 14 are a single fabricated component, some features of one component may extend through or blend into the other component. Therefore, it should be understood that the labels "body" and "clip" are merely explanatory and are not intended to rigidly define post 10.

Body 12 may be fabricated such that the ratio between the height and the cross-section favors the height. However, the ratio between the height and cross-section may be equal or may favor the cross-section, depending on the application, as will be evident from this disclosure. The cross-section of body 12 may be fabricated from a variety of shapes, including a quadrilateral (e.g., square, rectangle, diamond), a circle, a triangle, a balbis ("H-shape"), a cross ("plus sign"), among others, as will be apparent based on the intended purpose of this disclosure.

In an exemplary embodiment, body 12 has a height that is greater that the cross-sectional distance and a cross-section with a substantially cross shape ("plus sign"). Body 12 further includes at least one engagement feature. Engagement feature may include at least one slot 16 and at least one hole 24. At least one slot 16 is defined by two side walls 18, 20. At least one hole 24 may be centrally located on top face 26 and extend some distance inward from top face 26 to clip portion 14. Slot 16 may extend some distance from top surface 26 towards clip 14. In some embodiments, slot 16 extends from top surface 26 through at least a portion of clip 14. The depth of slot 16 may be further defined by the distance between face 22 and slot bottom 28. Slot 16 may be recessed a distance below top face 26, such that slot top 30 is the top of slot 16. The cavity between slot top 30 and top face 26 is configured and dimensioned to accept a portion of partition, further described below. Slot 16, as defined by side walls 18, 20 and slot bottom 28, may be square, rectangle, semi-circular, among other shapes.

Body 12 may further include additional engagement features. For example, alternatively located holes, dimples, slots, cavities, fasteners, etc., as can be appreciated in view of this disclosure. It is a desire to illustrate that post 10 and at least one partition may be releasably attached. As such, engagement features that provide attachment and detachment of at least one partition from post 10 are appreciated.

Figure 1A:
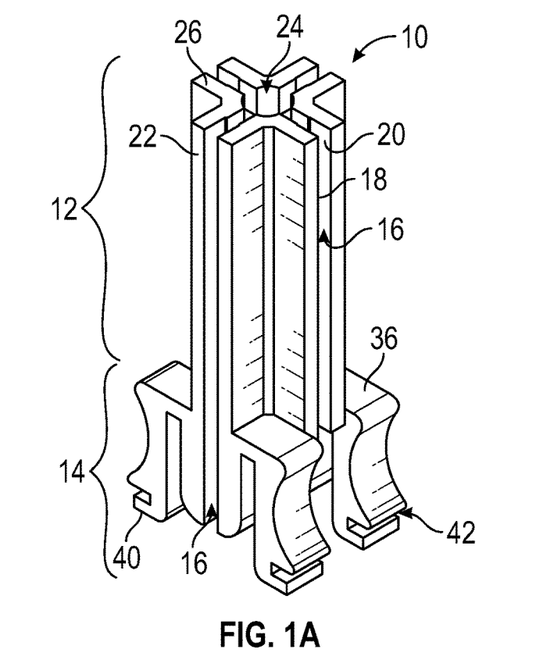
FIGS. 1A-1E schematically depict a post according to the present disclosure.
Figure 1B:
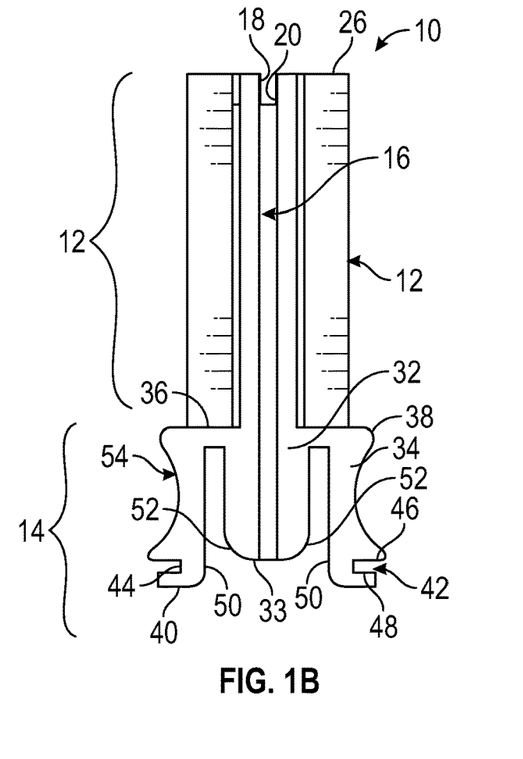
Figure 1C:
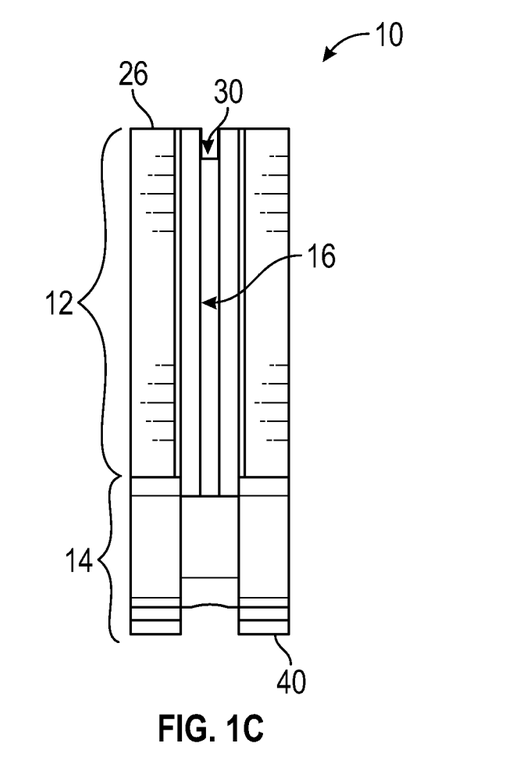
Figure 1D:
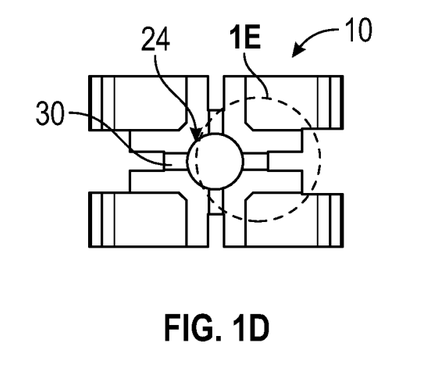
Figure 1E:
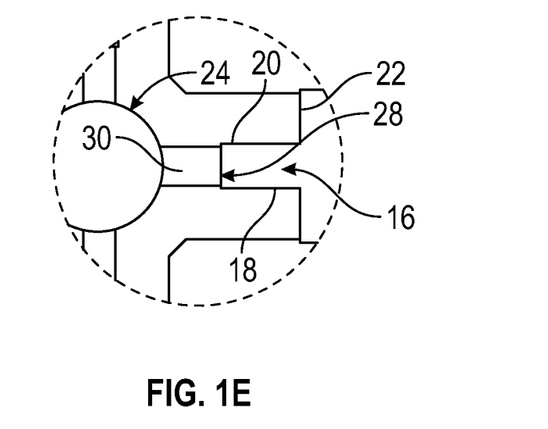

Clip 14 may include clip body 32 and two symmetrically adjacent arms 34, located on either side of clip body 32. Clip body 32 may be coplanar with face 22. In some embodiments, side walls 18, 20 and clip body 32 may be the same component, as depicted in FIGS. 1A-1C. In other embodiments, clip 14 may be a separate component, as described in U.S. Provisional Application No. 62/633,429, which is incorporated herein by reference. As mentioned above, slot 16 may extend at least partially through clip 14. In one embodiment, slot 16 may extend from top surface 26 through base 33 on clip body 32. Surface 36 connects arm 34 to clip body 32 by way of shoulder 38. Located above arm base 40 is cavity 42, which provides a tray attachment feature to directly or indirectly attach to at least one tray perforation (See, FIG. 8). The disclosed interface features of cavity 42 may include back face 44, upper face 46, and lower face 48, which collectively form cavity 42. In relation to back face 44, the length of lower face 48 may be shorter than the length of upper face 46, as depicted. Lower face 48 having a shorter length enables an easier installation and removal from tray perforations without sacrificing clip engagement. However, in another embodiment, upper face 46 and lower face 48 may have similarly dimensioned lengths.

In exemplary operation, at least a portion of cavity 42 captures a portion of a tray perforation. To ensure clip 14 does not shift after installation with the tray, back face 44 is under spring load in contact with an inside wall of a perforation. In one example, by simultaneously compressing arms 34, such that face 50 moves closer to outer face 52 on clip body 32, the distance between back face 44 on either arm 34 is shortened so that cavity 42 may be inserted into the respective perforations. Once arms 34 are released into their relaxed position, back face 44 will be in contact with an inside wall of a perforation, as discussed above. In another example, arms 34 are individually compressed so that face 50 moves closer to outer face 52 on clip body 32, and each individual cavity 42 is introduced into the respective perforation. Of note, attachment is not to be limited to the bottom of the tray (not shown); rather, attachment may further be accomplished with the sidewalls and the cover (not shown). For purposes of the present disclosure, when one of a tray, a sidewall(s) and/or a cover are mentioned, the others not mentioned are included, unless otherwise stated.

In an exemplary embodiment, arms 34 may include a semi-circular feature 54 located on the outside surface of arm 34, opposite surface 50. Semi-circular feature 54 may provide a specific location for a user to place their fingers to assist in compressing arms 34 for insertion or removal from a tray.

Various post assemblies may include at least one clip 14, described above, for direct or indirect attachment to a tray. However, in an exemplary embodiment, two clips 14 may be used to engage one post 10 with a sterilization tray. As previously mentioned, a partition may refer to a bracket and/or a divider. For merely an illustrative explanation, which is not intended to be limiting, a bracket, as used herein, refers to a component that directly/indirectly engages with a medical device. A divider, however, does not directly capture a medical device, but may be used to create a containment area (e.g., a square or rectangle) or separate an area. The disclosed bracket may further act as a divider. In any case, "partition" encompasses a "divider" and a "bracket" and the use of "divider" or "bracket" is merely to supplement "partition" for explanatory purposes only.

Figure 2A:
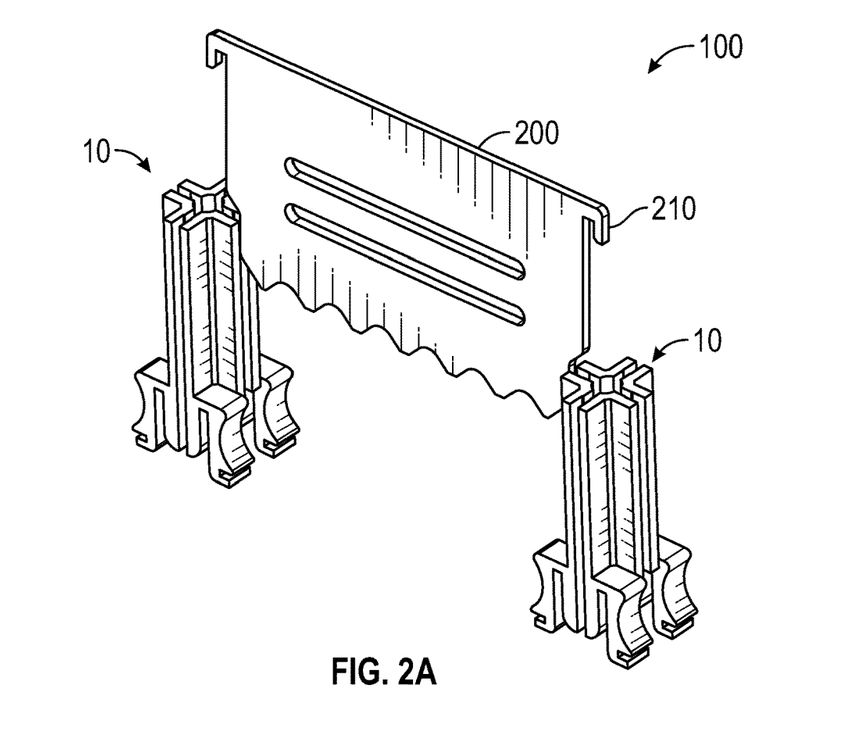
FIGS. 2A-2B schematically depict an unassembled and assembled post and divider assembly according to the present disclosure.
Figure 2B:
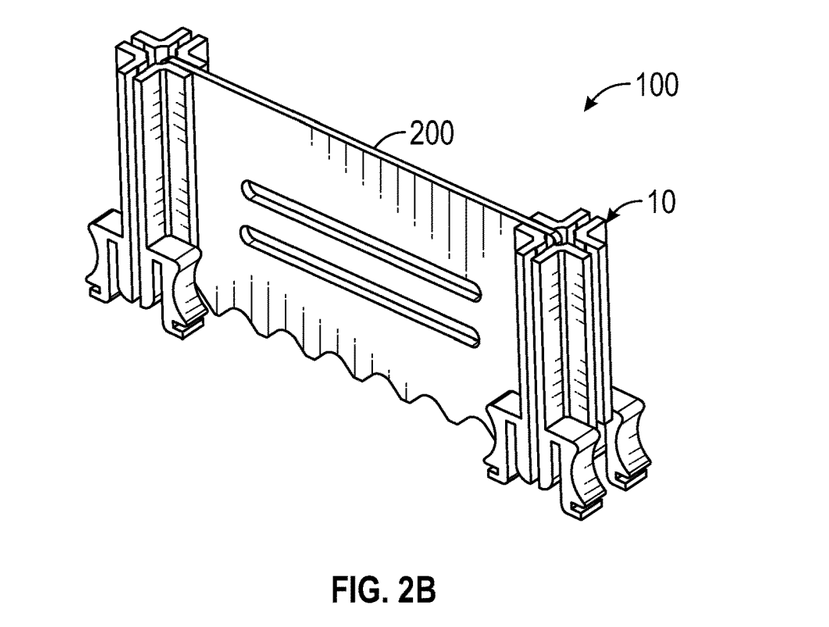

In an exemplary embodiment, at least two posts 10 may directly/indirectly engage with at least one partition (e.g., bracket and divider). FIG. 2A depicts a partially assembled post/partition assembly 100 utilizing dual posts 10 and partition (e.g., divider) 200. FIG. 2B depicts a fully assembled partition assembly 100. To better understand the interface between post 10 and partition, it is best to view FIGS. 2A and 2B with reference to post 10 (FIGS. 1A-1E) and partition (e.g., divider and bracket) figures (FIGS. 3 and 6).

Figure 3A:
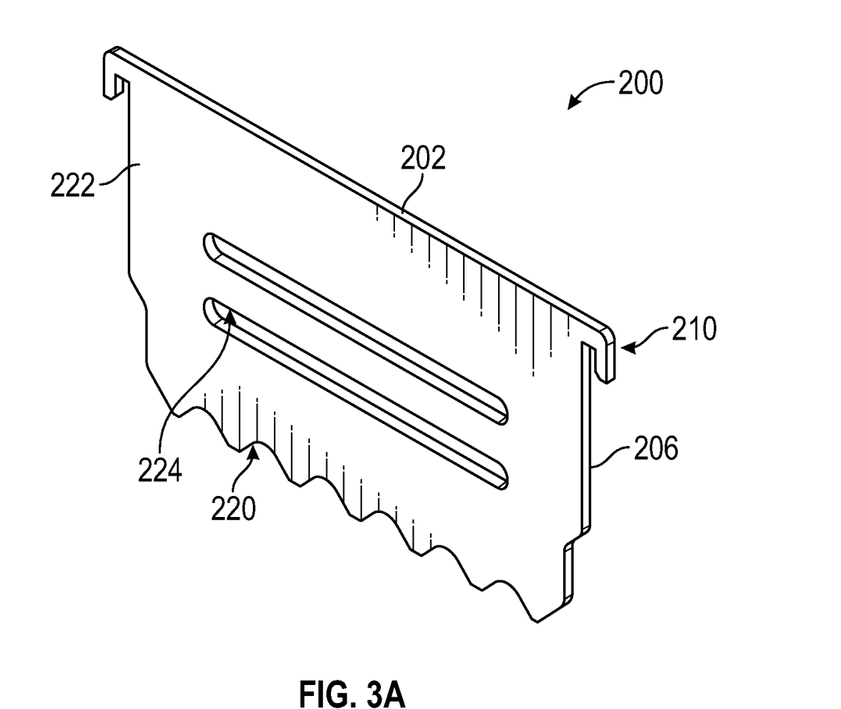
FIGS. 3A-3B schematically depict a divider according to the present disclosure.
Figure 3B:
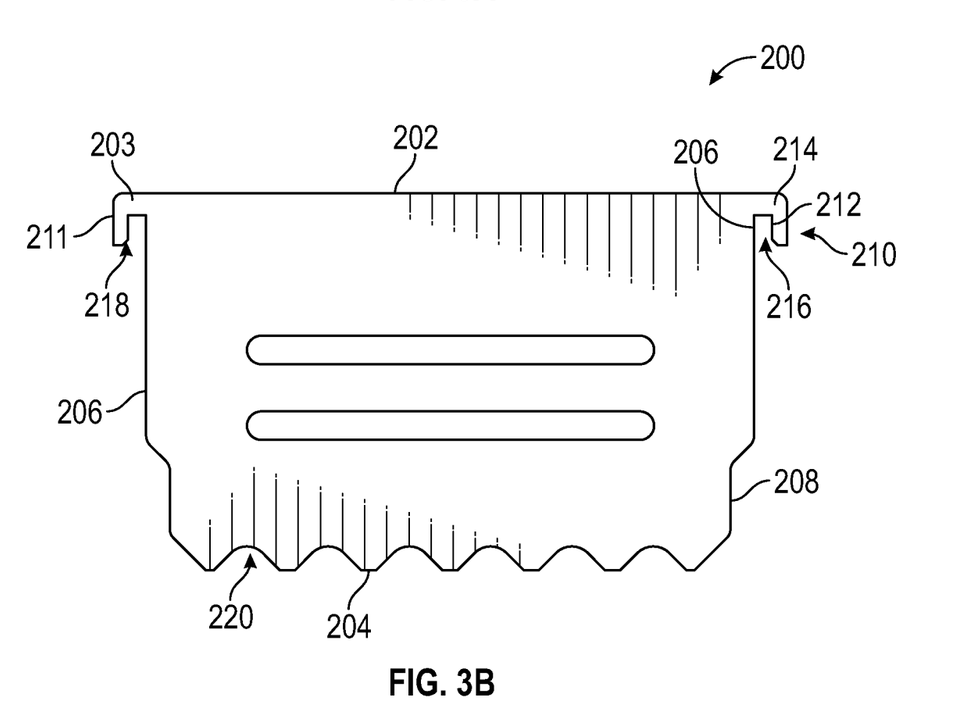

With reference to FIGS. 3A and 3B, divider 200 is defined by top surface 202, bottom surface 204 and sides 206. Divider 200 may include sides 206, which define a first width, and cutouts 208, which define a second width, wherein the second width is narrower than the first width.

Divider 200 may further include at least one engagement feature to interface with at least one post 10. In an exemplary embodiment, divider 200 includes at least one hook feature 210. Hook feature 210 may be situated at various positions along sides 206 based on the desired interface between divider 200 and post 10. Hook feature 210 may at least partially extend from top surface 202 and side 206 to form an overhang 203. Extension feature 211 may further extend from overhang 203 towards bottom surface 204, thereby at least partially forming cavity 216. Extension feature 211 may be substantially perpendicular to overhang 203. Extension feature 211 may be angled in relation to overhang 203. Extension feature further includes side 212, which, in addition to side 206 and cavity bottom 214, at least partially defines cavity 216. Extension feature 211 may further include an element to facilitate an easier installation and removal of hook feature 210 from hole 24 of post 10. Extension feature 211 may include a chamfered element 218 at the base of side 212.

Additional features may be incorporated into divider 200. For example, advantageous cutouts 220 may be incorporated into bottom surface 204. In doing so, the contact of bottom surface 204 with the top surface of the tray would be limited. However, cutouts 220 are not intended to be limited to those instances where bottom surface 204 interfaces with the top surface of a tray. Cutouts 220 may be a variety of shapes, including a square, triangle, rectangle, circle, oval, among others. In another example, bottom surface 204 remains intact and cutouts 220 are located some distance away from bottom surface 204. Additional cutouts 224 may be incorporated into divider face 222. Cutouts 224 may be a variety of shapes, including a square, triangle, rectangle, circle, oval, among others. Cutouts 220, 224 may enable sterilization materials to pass through (or under) divider 200 and into the area on the other side of divider 200.

Figure 4A:
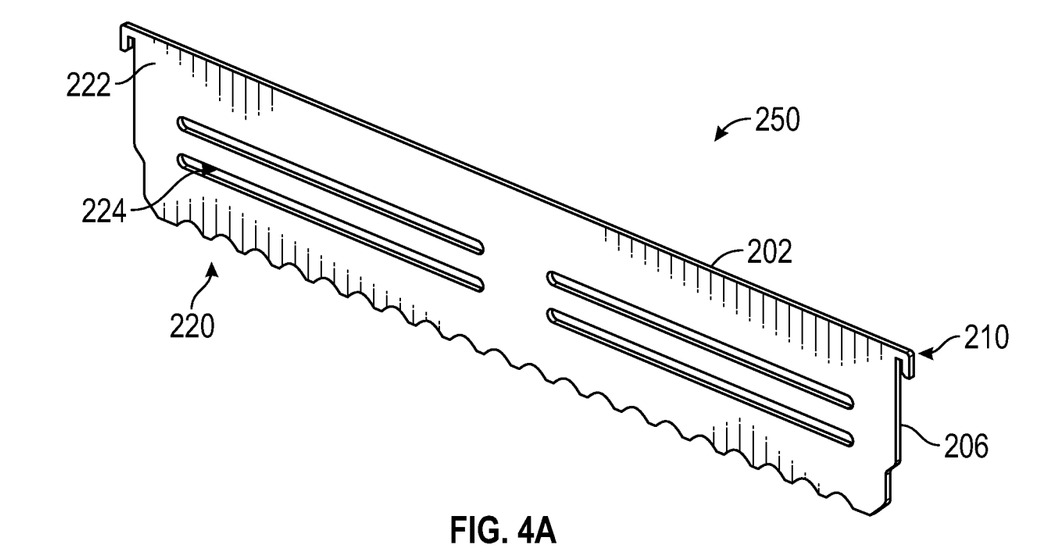
FIGS. 4A-4B schematically depict a divider according to the present disclosure.
Figure 4B:
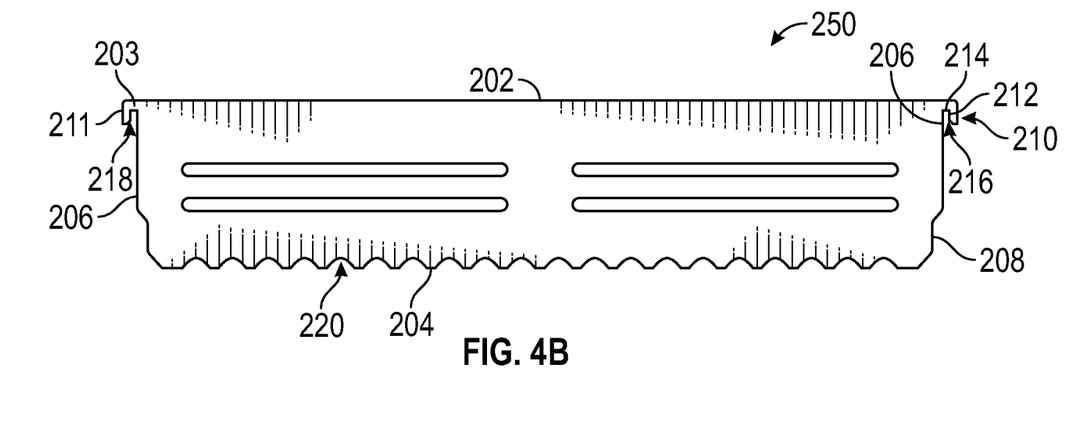

Divider 200 may be fabricated in a variety of lengths and heights. Utilizing the grid-based perforation pattern of a tray, divider 200 may be fabricated in a length that is consistent with the distance between perforations. A variety of lengths can be appreciated, including 20 slot divider 250, see FIG. 4, which, including two posts 10, encompasses the width of a standard sterilization tray. Aside from length, 20 slot divider 250 is very similar to divider 200, therefore, liked components are numbered. Divider 200, as depicted, is a 6 slot divider. The divider length may be between one slot to about forty slots, and every variation therebetween.

In an exemplary embodiment, as shown in FIGS. 2A-2B, divider assembly 100 includes two posts 10 and at least one divider 200, 250. In operation, posts 10 are positioned directly/indirectly in relation to a tray (not shown) at a distance consistent with the desired divider length. Side 206 of divider 200, 250 is aligned with slot 16 of post 10, such that cutout 208 is introduced first. Cutout 208 acts as a locating feature for insertion of divider 200, 250 into slot 16. In some embodiments, cutout 208 may not touch post 10 at all and is merely designed for gradual insertion/removal from slot 16. Once engaged, sides 206 slide within slot 16 until divider 200, 250 is fully engaged with post 10. Fully engaged may refer to an engagement feature and/or the end (e.g., bottom) of slot 16. Hook feature 210 may engage with hole 24 of post 10 to act as an engagement feature and semi-permanently constrain divider 200, 250 to post 10.

In another exemplary embodiment, with reference to FIGS. 5-7, partition (e.g., bracket) assembly 300 advantageously depicts a potential assembly including post 10, partition (e.g., bracket) 350 and bracket insert 400. Bracket assembly 300 is assembled substantially similar to FIG. 2, as described above.

Figure 6A:
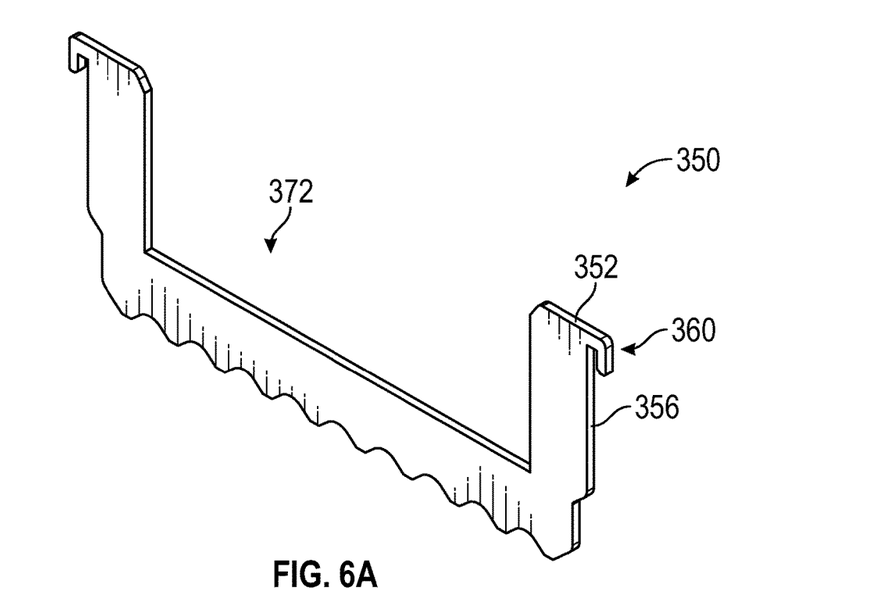
FIGS. 6A-6B schematically depict a bracket according to the present disclosure.
Figure 6B:
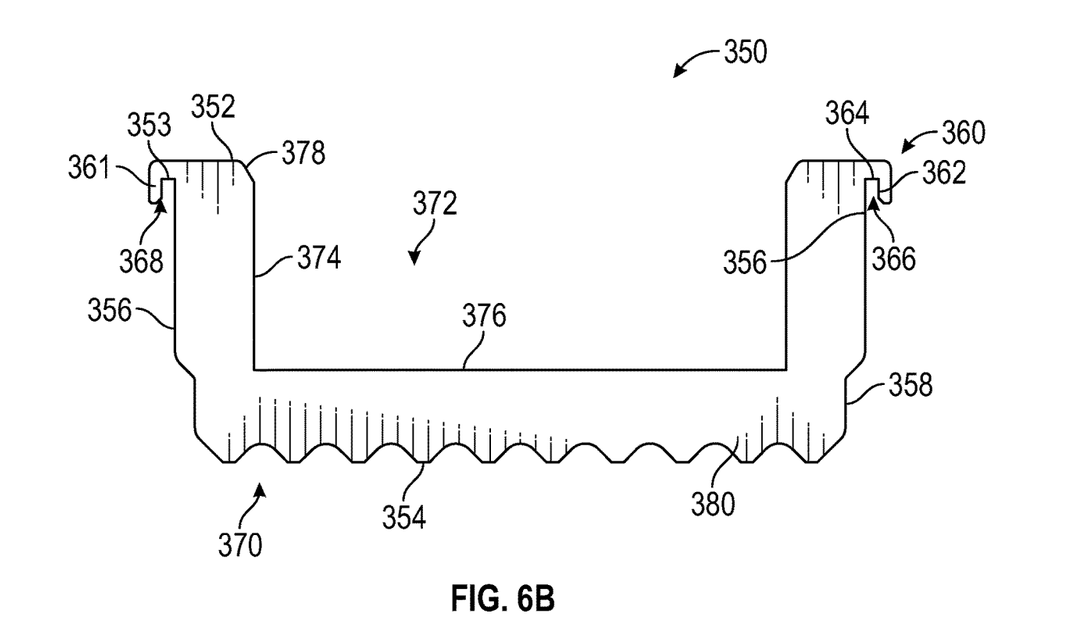

Bracket assembly 300 is best understood with reference to FIGS. 6 and 7. With reference to FIGS. 6A and 6B, bracket 350 is defined by top surface 352, bottom surface 354 and sides 356. Bracket 350 may include sides 356, which define a first width, and cutouts 358, which define a second width, wherein the second width is narrower than the first width.

Bracket 350 may further include at least one engagement feature to interface with at least one post 10. In an exemplary embodiment, bracket 350 includes at least one hook feature 360. Hook feature 360 may be situated at various positions along sides 356 based on the desired interface between bracket 350 and post 10. Hook feature 360 may at least partially extend from top surface 352 and side 356 to form overhang 353. Extension feature 361 may further extend from overhang 353 towards bottom surface 354, thereby at least partially forming cavity 366. Extension feature 361 may be substantially perpendicular to overhang 353. Extension feature 361 may be angled in relation to overhang 353. Extension feature further includes side 362, which, in addition to side 356 and cavity bottom 364, at least partially defines cavity 366. Extension feature 361 may further include an element to facilitate an easier installation and removal of hook feature 360 from hole 24 of post 10. Extension feature 361 may include a chamfered element 368 at the base of side 362.

Additional features may be incorporated into bracket 350. For example, advantageous cutouts 370 may be incorporated into bottom surface 354. In doing so, the contact of bottom surface 354 with the top surface of tray would be minimal. However, cutouts 370 may be included in instances where bottom surface 354 does not interface with the top surface of a tray. Cutouts 370 may be a variety of shapes, including a square, triangle, rectangle, circle, oval, among others. In another example, bottom surface 354 is unaffected and cutouts 370 are located some distance above bottom surface 354, towards top surface 352. Cutouts 370 may enable sterilization materials to pass through bracket 350 and into the area on the other side of bracket 350.

In an exemplary embodiment, as shown in FIGS. 5A-6B in view of FIGS. 2A-2B, with relation to divider assembly 100, bracket assembly 300 includes two posts 10 and at least one bracket 350. In operation, posts 10 are positioned directly/indirectly in relation to a tray (not shown) at a distance consistent with the desired bracket length. Side 356 of bracket 350 is aligned with slot 16 of post 10, such that cutout 358 is introduced first. Cutout 358 acts as a locating feature for insertion of bracket 350 into slot 16. In some embodiments, cutout 358 may not touch post 10 at all and is merely designed for gradual insertion/removal from slot 16. Once engaged, sides 356 slide within slot 16 until bracket 350 is fully engaged with post 10. Fully engaged may refer to insertion of an engagement feature and/or bracket 350 "bottoming out" at the end of slot 16. In an exemplary embodiment, hook feature 360 may engage with hole 24 of post 10 to act as an engagement feature and to semi-permanently constrain bracket 350 to post 10.

As previously stated, bracket 350 may further include features to directly/indirectly capture medical devices. In one embodiment, bracket 350 includes features to capture medical devices. Bracket 350 may feature variously sized U-shaped or partially U-shaped cavities (not shown), i.e., attachment features, fabricated within. U-shaped cavities (not shown) may capture the exterior surface of a reusable medical device for retention to a tray. U-shaped cavity (not shown) may be used to capture the handle of a reusable medical device (not shown). Conversely, U-shaped cavity (not shown) may be used to capture the tool portion of a reusable medical device (not shown).

Bracket 350 may be fabricated in a variety of lengths and heights. Utilizing the grid-based perforation pattern of a tray, bracket 350 may be fabricated in a length that is consistent with the distance between perforations. A variety of lengths can be appreciated, including a one slot bracket 350 to about forty slots bracket 350, and every variation therebetween. For example, a 20 slot bracket, including two posts 10, fills the width of a standard sterilization tray.

In yet another embodiment, bracket 350 includes cavity 372, which is configured and dimensioned to accept at least one insert (See, e.g., FIG. 7). Cavity 372 is defined by cavity sidewall 374 and cavity base 376. The dimensions of cavity 372 may be smaller than the perimeter dimensions of insert 400, as discussed below. Feature 378 may assist with assembling bracket 350 with insert 400.

Figure 7A:
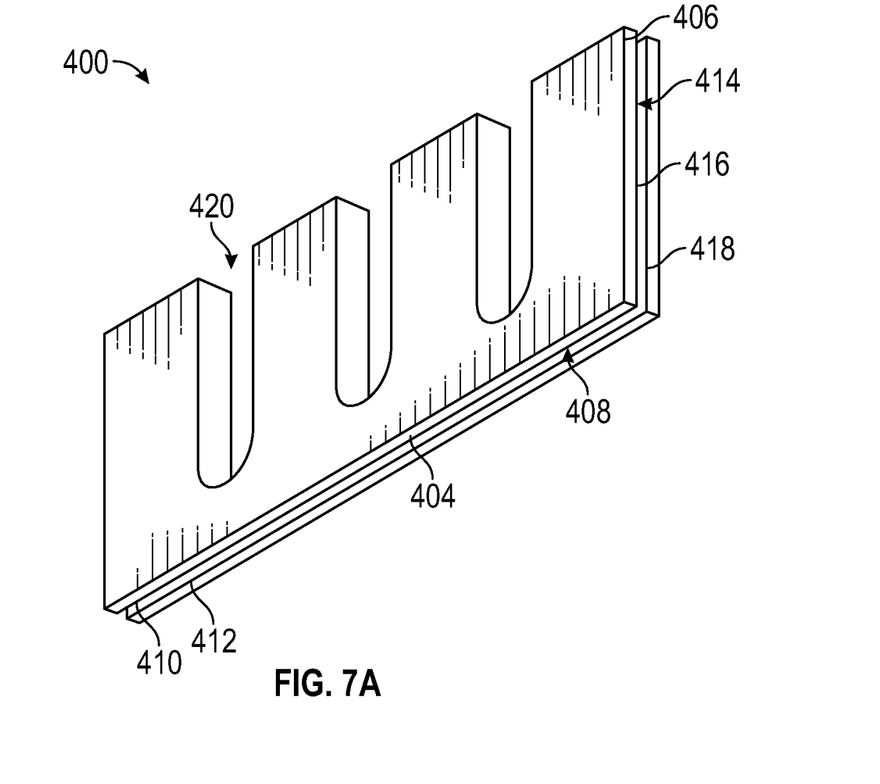
FIGS. 7A-7B schematically depict an insert according to the present disclosure.
Figure 7B:
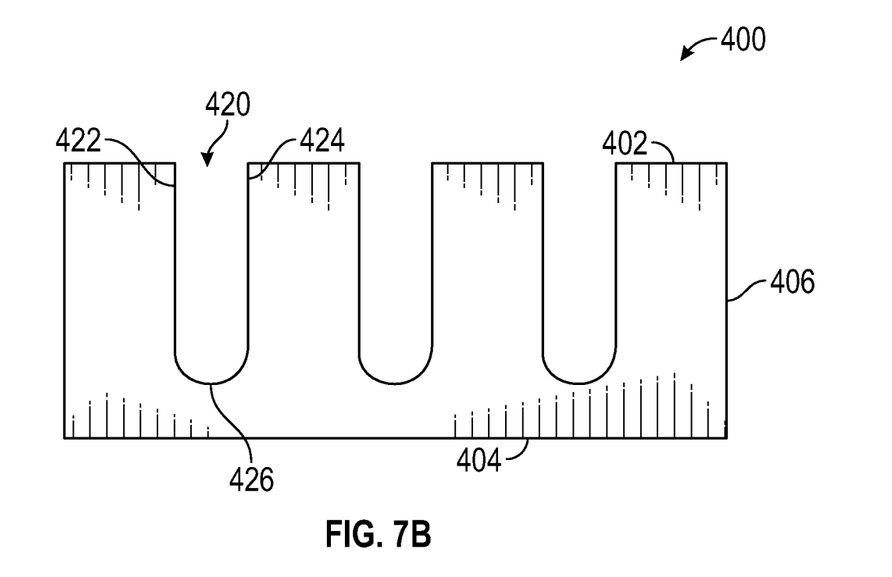

Insert 400 is defined by top surface 402, bottom surface 404 and sides 406. Located on bottom surface 404 and sides 406 are slots 408, 414 for releasable engagement with bracket 350. Slot 408 is at least partially defined by sidewalls 410, 412 and a base (not shown). Similarly, slot 414 is at least partially defined by sidewalls 416, 418 and a base (not shown). The distance between sidewalls 410, 412 and 416, 418 is at least equivalent to the thickness of bracket 350. The distance between sidewalls 410, 412 and 416, 418 may at least be slightly larger than the thickness of bracket 350. However, if the material of insert 400 is substantially malleable then the distance between sidewalls 410, 412 and 416, 418 may be slightly smaller than the thickness of bracket 350. The depth of slot 414 may be at least the distance between cavity sidewalls 374. The depth of slot 408 may be at least sufficient for top surface 402 of inset 400 to be planar with top surface 352 of bracket 350. It should be appreciated, however, that the depth of slot 408, 414 may be larger or smaller than described above such that insert 400 is set further within cavity 372 or extends past the edges of cavity 372.

Insert 400 may further include at least one attachment feature to capture medical devices. Insert 400 may feature variously sized U-shaped or partially U-shaped cavities 420 fabricated within. U-shaped cavity 420 are defined by sidewalls 422, 424 and base 426. The dimensions of U-shaped cavity 420 may be altered to accommodate a variously-sized medical devices. U-shaped cavity 420 may capture the exterior surface of a reusable medical device for retention to a tray. U-shaped cavity 420 may be used to capture the handle of a reusable medical device (not shown). Conversely, U-shaped cavity 420 may be used to capture the tool portion of a reusable medical device (not shown). Insert 400 may include at least one U-shaped cavity 420, however, the quantity of cavities 420 is merely limited by the dimensions of insert 400.

Although described as U-shaped cavities, it is appreciated that additional designs may be used, for example, substantially quadrilateral (e.g., square, rectangular, diamond). Further, the cavities included within bracket 350 and/or insert 400 are not limited to one dimension and each cavity may be a different dimension, depending on the desired medical device. In another embodiment, the disclosed cavities may be located at different positions (e.g., planes, heights) within bracket 350 and insert 400. For example, when fully assembled with medical devices, various medical devices may be located at different heights within bracket 350 and insert 400. Specifically, one medical device may be located at a first height, a second medical device may be located at a second height, and a third medical device may be located at a third height, and so on, wherein the first height is closer to top surface 352, 402 of bracket 350/insert 400 than the second and third heights.

Figure 5A:
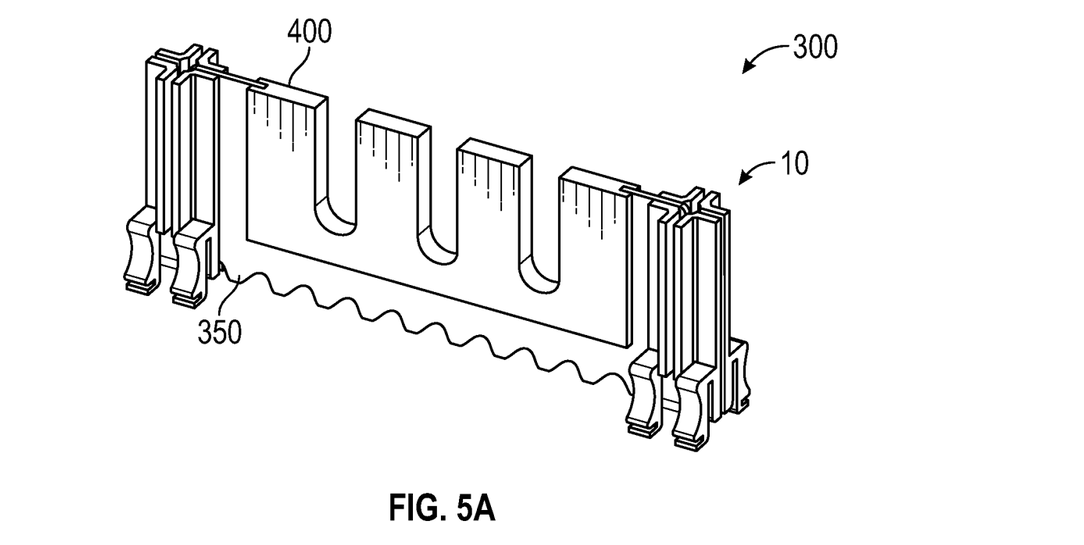
FIGS. 5A-5B schematically depict an assembled post and bracket assembly according to the present disclosure.
Figure 5B:
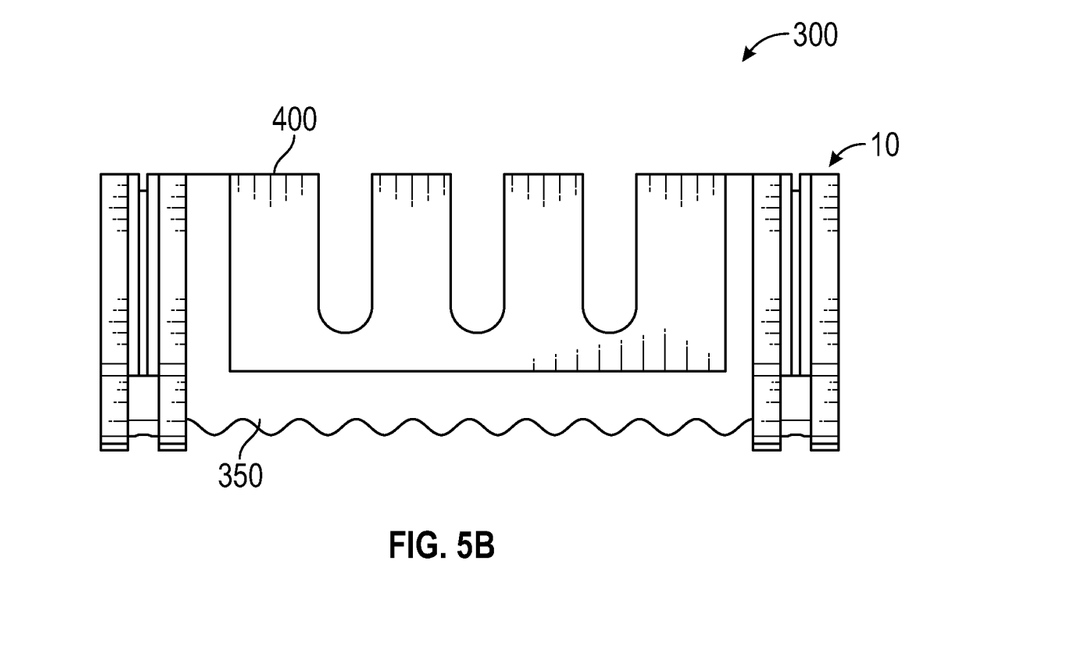

Insert 400 may be assembled with bracket 350 in a semi-permanent configuration. In an exemplary embodiment, insert 400 is assembled with bracket 350 such that slot 408 directly/indirectly engages with cavity base 376 and slot 414 directly/indirectly engages with cavity side 374. Particularly, the portion of slot 414 that is closest to bottom surface 404 may be insert into cavity 752, wherein slot 414 engages with cavity sidewalls 374. Insert 400 may be slid along cavity sidewalls 374, wherein slot 414 maintains at least partial contact with cavity sidewalls 374, until bottom surface (not shown) of slot 408 at least partially interfaces with cavity bottom 376. As depicted in FIGS. 5A and 5B, top surface 402 of insert 400 may be substantially coplanar with top surface 352 of bracket 350. However, as discussed above, top surfaces 352 and 402 do not have to align for insert 400 to be correctly and fully assembled.

The disclosed posts/partitions (e.g., dividers/brackets), i.e., tray components, may be fabricated from a material that is impervious to the harsh conditions of central sterile processing processes. However, materials that are not impervious to the conditions of central sterile processing processes may be coated so as to make them resistant, i.e., able to withstand sterilization conditions (e.g., coating, anodizing, and/or plating). The disclosed tray components may be fabricated from plastic, silicone, or metal (e.g., aluminum). In an exemplary embodiment, tray components may be fabricated from a thermoplastic, e.g., Radel® (Solvay S. A., Brussels, Belgium, Tecapro® (Ensinger GmbH, Nufringen, Germany), and Propylux® (Westlake Plastics, Lenni, Pa.).

The disclosed tray components may be color-coded and/or include other indicia so as to quickly notify a user specific information about the reusable medical device/instrument. In one example, since a surgery may include several trays of surgical reusable medical devices, a color may signify a specific step in the surgical process, e.g., blue refers to the first step in a surgery, green refers to the second, and so on. In another example, the color of the bracket may refer to a specific reusable medical device, e.g., pink refers to a driver, yellow refers to a scissors, and so on. For purposes of the foregoing color-coded examples, alternative indicia may be employed, e.g., numerical indicia imprinted on the brackets, coded-protuberances, lettering, or other physical indicia formed on or mounted to the tray components, or the like.

In another exemplary embodiment, at least one tray component may include at least one feature to track a reusable medical device/instrument and notify a user of an event, e.g., embedded electrical connection. In one example, when a conductive portion (or feature) of a reusable medical device/instrument makes contact with the embedded electrical connection, the circuit may be completed and information specific to that reusable medical device/instrument may be transferred to a user. For example, a reusable medical device/instrument may have specific electrical characteristics such that a disclosed tray component may be adapted to track the presence/absence of the reusable medical device/instrument. In such case, when the reusable medical device/instrument is removed from the at least one tray component, a signal may be sent to a processor/recording software to notify that such reusable medical device/instrument has been removed. The disclosed tracking functionality may assist in compliance with Unique Device Identification ("UDI") protocols, currently in development with the U.S. Food & Drug Administration. In another example, the disclosed tray component may include inscribed identification reading capabilities, e.g., QR code or barcode, so as to "read" the presence of a reusable medical device/instrument that is outfitted with an inscribed identification feature. The disclosed inscribed identification feature may include information about a surgery, a patient, a hospital, and the like, among other important identification information.

Figure 8:
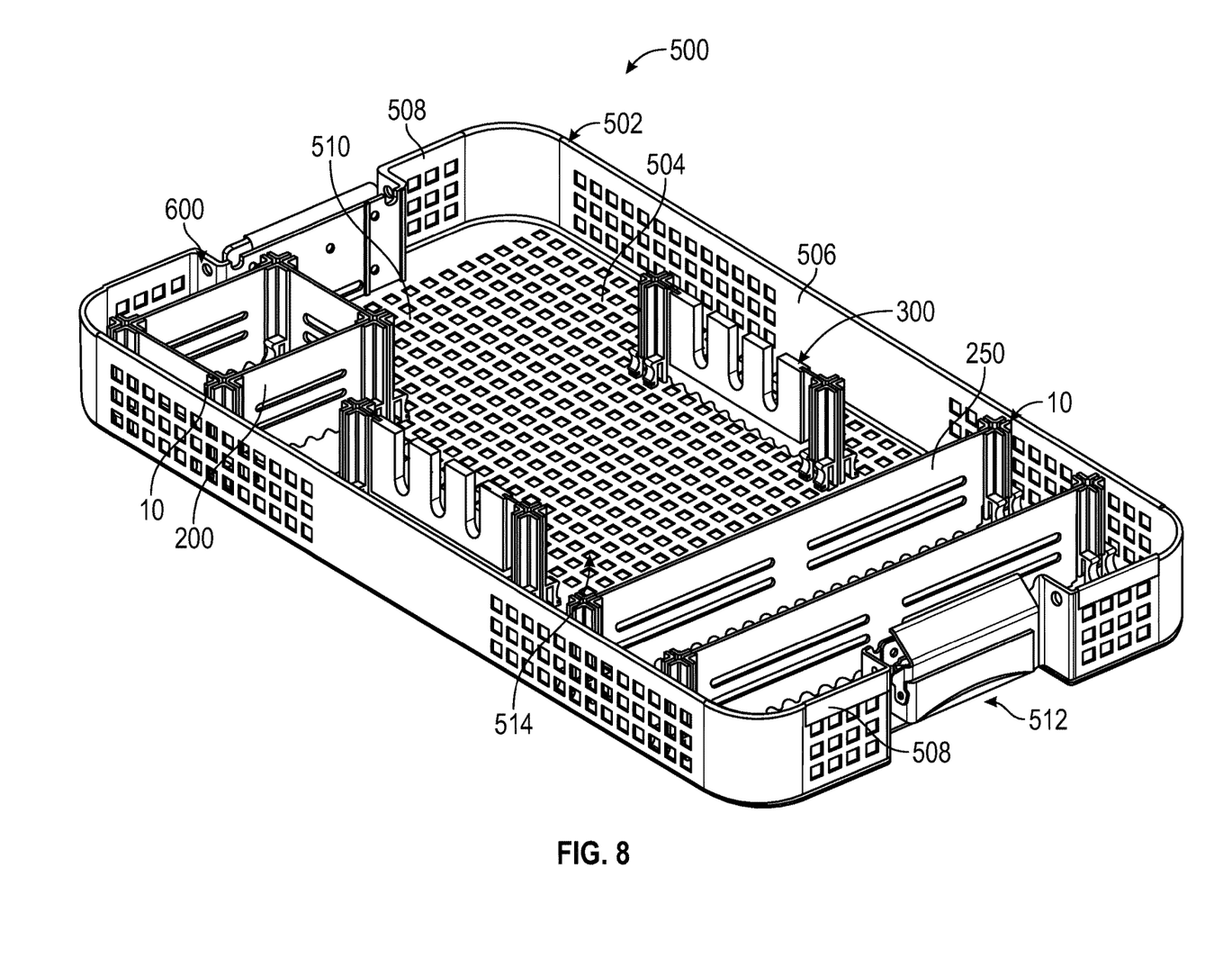
FIG. 8 schematically depicts an assembled perspective view of an exemplary modular tray and post assembly, according to the present disclosure.

With reference to FIG. 8, tray assembly 500 advantageously depicts a potential layout of various post and post and partition assemblies 10, 200, 250, 300, 600 mounted in relation to tray 502. The interface between post and post and partition assemblies 10, 200, 250, 300, 600 and tray 502 was discussed with reference to post 10. Of note, although assembly 500 depicts a layout of various post and post and partition assemblies 10, 200, 250, 300, 600, the layout is merely illustrative of one potential surgical procedure and does not limit the scope of this disclosure. Furthermore, the quantity and placement of post and post and partition assemblies 10, 200, 250, 300, 600 and those variations not depicted but previously referenced, may vary without departing from the spirit/scope of this disclosure.

With reference to FIG. 8 tray 502 includes base 504 and sidewalls 506, 508. Sidewalls 506, 508 extend perpendicularly from base 504 thereby defining inside volume 510 of tray 502. Inside volume 510 may vary depending on the dimensions of tray 502. Any dimensions discussed in this disclosure are merely for facilitating discussion and are not meant to be limiting. Sidewalls 506, 508 may be fabricated with base 504 or may be separate components that are directly or indirectly attached to base 504. Sidewalls may be at a height that is taller than tray components installed within tray 502. Base 504 may further include features, e.g., feet, (not shown) that may raise base 504 some distance away from a working surface. The quantity of feet (not shown) may vary depending on the intended design, but enough feet (not shown) should be used to ensure assembly 500 is even and steady. Feet (not shown) may be fabricated with base 504 or may be separate components that are directly or indirectly attached to base 504. In one example, feet (not shown) are installed beneath base 504 by a fastener (e.g., screw, pin, rivet, etc.) or other conventional attachment methods (e.g., welding).

Base 504, sidewalls 506, 508, and feet (not shown) may be fabricated from a material selected from metal, silicone, plastic (e.g., thermoplastic), as will be apparent to those skilled in the art. For those applications where tray 502 will be exposed to harsh conditions, e.g., an autoclave, materials that can withstand increased heat, humidity, and pressure should be used. However, for those materials that cannot withstand those conditions, a coating should be applied, e.g., anodized coating on metal surfaces. Sidewalls 506, 508 may be attached using conventional attachment methods that are consistent with the material of base 504 and sidewalls 506, 508, e.g., welding, mechanical attachment, adhesives, fasteners, or a combination thereof.

Sidewalls 506, 508 may be substantially planar or may further include feature(s) that cause sidewalls 506, 508 to be nonplanar. The noted feature(s) may be fabricated within or associated with sidewalls 506, 508 and may extend outwardly or inwardly of inside volume 510 of tray 502. In an exemplary embodiment, tray 502 includes handle 512, integrated within one or both sidewalls 506, 508. Tray 502 may further include identifying information. The information may include surgery number, patient name, reusable medical devices included within tray 502, hospital name, doctor name, among others, as will be known to one skilled in the art.

In yet another exemplary embodiment, tray 502 may further include features for stacking additional trays 502. Trays 502 may be stacked so that each base 504 is parallel with each base 504 above or below. The disclosed features may be incorporated within sidewalls 506, 508. For example, tabs (not shown) may be incorporated in sidewalls 506, 508 for engagement with base 504 of tray 502 stacked above. Specifically, tabs (not shown) may engage with perforations 514 of base 504. Further, when two or more trays 502 are stacked, with the lowest tray referenced as "A" and the tray above referenced as "B", and so on (C, D, . . . X), base 504 of tray B may be used as the cover of tray A, and so on for each stacked tray. The top tray X may have a cover, as described below.

Tray 502 may further include a plurality of perforations 514, as mentioned above. Perforations 514 may be located on base 504, sidewalls 506, 508, and/or cover (not shown). In exemplary embodiments, perforations are quadrilateral (e.g., square, rectangle, diamond) in geometry. Perforations 514 may be used to expose the contents of tray 502 to perioperative and central sterile processing process and/or for retention of tray component assemblies 10, 200, 250, 300, 600. However, perforations 514 may have additional uses without departing from the spirit/scope of this disclosure. Perforations 514 may further be aligned in a grid-based pattern to facilitate ease of bracket positioning, wherein perforations 514 may be of even distance between adjacent perforations 514. In an exemplary embodiment, a plurality of perforations 514 are square in shape and are located on base 504 and sidewalls 506, 508, in a grid-based pattern. Such grid-based pattern enables consistent and easily locatable positions for modular bracket assemblies, as discussed below.

Tray 502 may further include unique characters, e.g., alphanumeric characters, to signify horizontal and vertical perforations 514 for ease of bracket positioning. In one example, horizontal perforations 514 may be referenced by letters (e.g., A, B, C . . . etc.) and vertical perforations 514 may be referenced by numbers (e.g., 1, 2, 3 . . . etc.). In another example, horizontal perforations 514 may be referenced by numbers (e.g., 1, 2, 3 . . . etc.) and vertical perforations 514 may be referenced by letters (e.g., A, B, C . . . etc.). Regardless of character choice, horizontal and vertical perforations 514 may be the same or different character type, thereby creating a coordinate system for pinpointing a specific perforation, or series of perforations, on a grid. In doing so, the location of one or more tray component assemblies 10, 200, 250, 300, 600 will easily be determined. The above-described characters may be inscribed on base 504, adjacent to the outermost horizontal and vertical row/column of perforations 514 of tray 502 (or sidewalls 506, 508, or cover). Such positioning capabilities may be useful for a medical professional to quickly locate a reusable medical device during surgery and/or during inventory storage (and for access/location thereof).

Assembly 500 may further include a cover (not shown) to encase the components housed within tray 502. In one example, the disclosed cover may be a separate component of tray 502 that is entirely removable and is in contact with sidewalls 506, 508. In another example, the disclosed cover is hingedly attached to tray 502 such that the contents housed within tray 502 are accessible when said cover is open, but, when open, the cover continues to remain at least partially in contact with tray 502. The disclosed cover may be removable from tray 502 by removing at least a portion of the hinges. The disclosed cover may include perforations, as described above, and may further include brackets for retention of reusable medical devices. In an exemplary embodiment, the disclosed cover includes features that enable stacking of additional trays. Features may be incorporated into the exterior of cover (not shown) that capture feet (not shown), for example, indentations or clips.

As mentioned above, post and post and partition assemblies 10, 200, 250, 300, 600, among others, may be directly or indirectly mounted in relation to tray 502. In an exemplary embodiment, post and post and partition assemblies 10, 200, 250, 300, 600, among others, may be mounted in relation to perforations 514 of base 504. The disclosed attachment may be accomplished, for example, by post 10, depicted in FIG. 1, and more specifically, by clip 14. As mentioned above, clip 14 may be fabricated with post 10 or may be a separate component that is associated with any modular post/partition (e.g., divider/bracket) system, disclosed herein, or other partition design.

Figure 9:
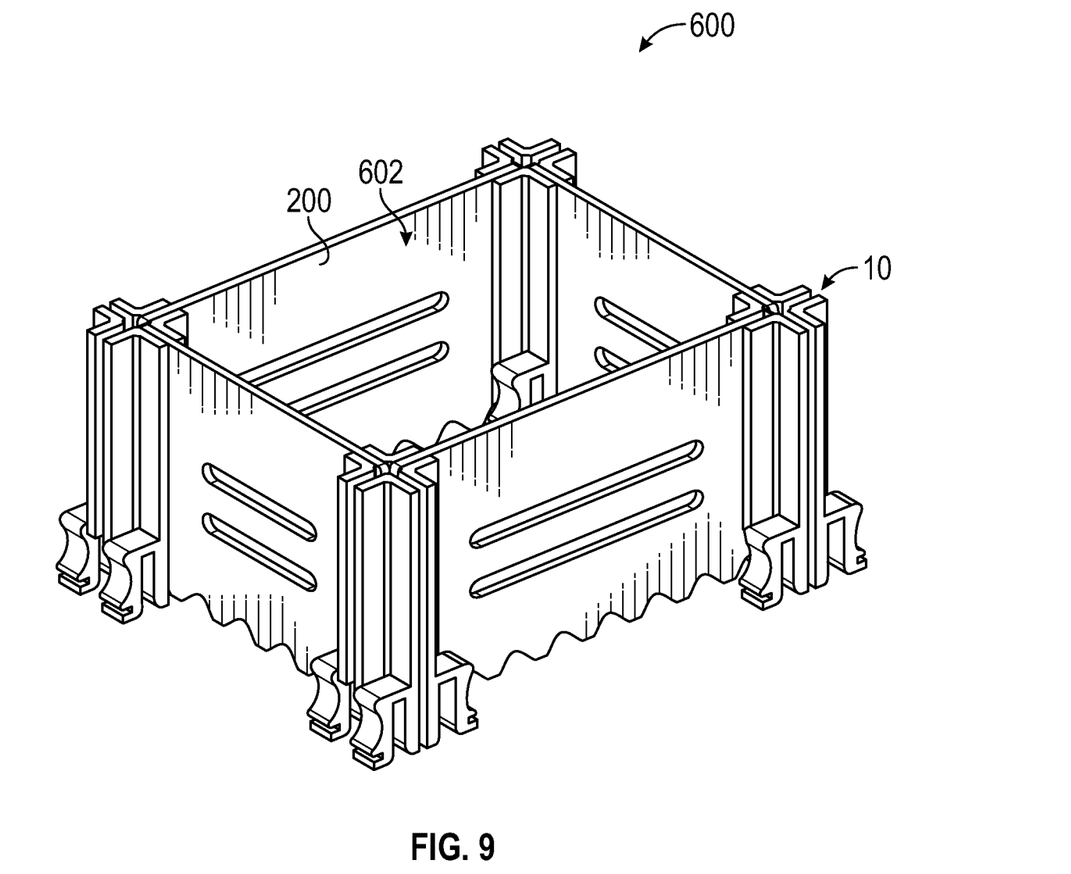
FIG. 9 schematically depicts a perspective view of a divider assembly according to the present disclosure.

As previously discussed, partition (e.g., divider) 200 may be positioned to form a containment area and/or separate one area from another. As depicted in FIG. 9, four partitions (e.g., dividers) 200 are positioned between four posts 10, as explained above, to form a containment area. Containment area, as depicted, forms volume 602, the quantity of which is dependent on the size dividers 200 and location of posts 10 in relation to the tray. Although depicted as four dividers 200, at least one of divider 200 may be substituted with at least one bracket.

Although the present disclosure has been described with reference to exemplary implementations, the present disclosure is not limited by or to such exemplary implementations. Rather, various modifications, refinements and/or alternative implementations may be adopted without departing from the spirit or scope of the present disclosure.

The invention claimed is:

1. A modular post assembly, comprising:
    at least one post that includes (i) a top surface defining a hole that extends downward from the top surface and (ii) four side faces, each of the four side faces defining an elongated slot that extends along and opens outwardly relative to said side face, wherein the hole is positioned inward of the elongated slots defined by the respective side faces;
    a partition detachably mounted relative to the at least one post, the partition including a partition body and an engagement hook extending from an end surface of the partition body;
    wherein when the partition is detachably secured relative to the at least one post, the engagement hook of the partition is secured within the hole of the at least one post and the end surface of the partition is positioned within the elongated slot of the at least one post, and
    wherein when the partition is detachably secured relative to the at least one post, the hole defined by the at least one post maintains sufficient space to accommodate engagement with at least three additional hooks associated with three distinct partitions positioned within elongated slots other than the elongated slot within which the partition is positioned.

2. The modular post assembly of claim 1, further comprising at least one tray attachment feature configured and adapted to interface with at least one tray perforation.

3. The modular post assembly of claim 2, wherein the at least one tray attachment feature is positioned on a clip, wherein the clip comprises a body, at least two arms located on either side of the body, and a shoulder which connects the body to the at least two arms, wherein the tray attachment feature is located opposite the shoulder on the arms, the arms, when compressed towards the body, engage the tray attachment feature with the at least one tray perforation.

4. The modular post assembly of claim 2, wherein the tray attachment feature is under spring force with the at least one tray perforation.

5. The modular post assembly of claim 1, further comprising a clip which comprises a body, at least two arms located on either side of the body, and a shoulder which connects the body to the at least two arms, wherein a tray attachment feature is located opposite the shoulder on the arms, the arms, when compressed towards the body, engage the tray attachment feature with at least one tray perforation.

6. The modular post assembly of claim 1, wherein the partition is releasably engaged with the at least one post.

7. The modular post assembly of claim 1, wherein up to four partitions are mounted with respect to the at least one post.

8. The modular post assembly of claim 1, wherein the partition further comprises an insert.

9. The modular post assembly of claim 1, wherein the partition further comprises an insert that releasably engages with the post.

10. The modular post assembly of claim 1, wherein the partition further comprises at least one attachment feature to engage with at least one medical device.

11. A modular post assembly of claim 10, wherein the attachment feature is selected from a group consisting of a U-shaped cavity, a partial U-shaped cavity, a slot, a cavity, and any combination thereof.

12. The modular post assembly of claim 1, wherein the at least one post and the partition are fabricated from a material selected from the group consisting of plastic, silicone, metal, and any combination thereof.

13. A modular post assembly of claim 12, wherein the at least one post and the partition are fabricated from a thermoplastic.

14. A modular post assembly of claim 1, wherein at least one of the at least one post and the partition is color-coded to a specific instance or device.

15. A modular post assembly of claim 1, wherein the partition includes an embedded electrical connection that completes a circuit when a reusable medical device is placed in contact therewith.

16. A modular post assembly of claim 1, wherein the partition includes an inscribed identification feature selected from a group consisting of QR code, barcode, and any combination thereof.

17. A modular post assembly of claim 1, wherein the at least one post comprises a first post and a second post;
    wherein the partition further comprises a second hook that extends from an end opposite the hook; and
    wherein the second hook is configured and adapted to engage with the second post.

18. A modular post assembly of claim 1, wherein the at least one post has a square cross-section.

19. A modular post assembly of claim 1, wherein the at least one post has a cross-shaped cross-section.

* * * * *